(12) United States Patent
Martin (10) Patent No.: US 10,350,103 B2
(45) Date of Patent: Jul. 16, 2019

(54) SPRAY FOAM SPLINT

(71) Applicant: Kevin D. Martin, El Paso, TX (US)

(72) Inventor: Kevin D. Martin, El Paso, TX (US)

(73) Assignee: The United States of America, as represented by the Secretary of the Army, Washington, DC (US)

( * ) Notice: Subject to any disclaimer, the term of this patent is extended or adjusted under 35 U.S.C. 154(b) by 463 days.

(21) Appl. No.: 15/168,639

(22) Filed: May 31, 2016

(65) Prior Publication Data

US 2016/0317343 A1    Nov. 3, 2016

Related U.S. Application Data

(62) Division of application No. 13/988,260, filed as application No. PCT/US2010/057240 on Nov. 18, 2010, now Pat. No. 9,427,489.

(51) Int. Cl.
| | | |
|---|---|---|
| *A61F 13/04* | (2006.01) |
| *A61F 5/058* | (2006.01) |
| *A61F 5/01* | (2006.01) |
| *A61L 15/14* | (2006.01) |
| *A61F 13/00* | (2006.01) |
| *A61G 1/04* | (2006.01) |
| *A61L 15/12* | (2006.01) |

(52) U.S. Cl.
CPC ............ *A61F 5/05841* (2013.01); *A61F 5/01* (2013.01); *A61F 5/058* (2013.01); *A61F 13/00063* (2013.01); *A61F 13/00085* (2013.01); *A61G 1/04* (2013.01); *A61L 15/12* (2013.01); *A61L 15/14* (2013.01); *A61F 2013/00106* (2013.01)

(58) Field of Classification Search
CPC ........ A61F 5/05841; A61F 5/01; A61F 5/058; A61F 13/00063; A61F 13/00085; A61F 2013/00106; A61F 13/04; A61F 5/05; A61F 13/041; A61F 2210/0085; A61F 5/0102; A61G 1/04; A61L 15/12; A61L 15/14; A61L 5/01
See application file for complete search history.

(56) References Cited

U.S. PATENT DOCUMENTS

| | | | | |
|---|---|---|---|---|
| 3,301,252 A | * | 1/1967 | Mahoney, Jr. | .......... A61F 13/04 602/8 |
| 4,538,601 A | * | 9/1985 | Barker | ................ A61F 5/05883 602/18 |
| 2003/0073942 A1 | * | 4/2003 | Gibbs | ..................... A61F 5/028 602/19 |

* cited by examiner

*Primary Examiner* — Ophelia A Hawthorne
(74) *Attorney, Agent, or Firm* — Elizabeth Arwine; William Eshelman (57) ABSTRACT

Orthopedic splinting materials and methods for stabilizing an injured limb or extremity of a human or animal are disclosed. The methods include applying a foam to the limb or extremity and allowing the foam to set to sufficient rigidity. A kit for stabilizing an injured limb or extremity includes a dispenser for a foamable composition. A spine board and method of making the spine board are disclosed. In situ preparation and application of a compression bandage are disclosed.

14 Claims, 4 Drawing Sheets

SPRAY FOAM SPLINT

FEDERALLY-SPONSORED RESEARCH AND DEVELOPMENT

This invention is assigned to the United States Government. Licensing inquiries may be directed to Intellectual Property Office, USAMRMC, 504 Scott Street, Fort Detrick, Md., 21702-5012. Tel: (301) 619-7808. Fax (301) 619-5034. E-mail: Elizabeth.Arwine@amedd.army.mil. Reference Army Case No. WBAMC 09-25.

BACKGROUND

This disclosure related to orthopedic splinting materials and methods for using a fast setting rigid spray foam, and may optionally comprise spraying the foam directly onto a fractured extremity without the use of pre-wraps.

SUMMARY

The present subject matter related to orthopedic splinting materials and methods for stabilizing an injured limb or extremity of a human or animal comprising applying a foam to the limb or extremity and allowing the foam to set to sufficient rigidity. In some embodiments, the foam is sprayed directly on the skin and does not produce an amount of heat release that is painful or uncomfortable on the skin. In certain embodiments, the foam sets to sufficient rigidity in less than 60 seconds. In a specific embodiments, the foam is a Spray Polyurethane Foam (SPF) that sets in less than 60 seconds and does not produce an amount of heat release that is painful or uncomfortable on the skin. Also provided is a one-step method for stabilizing an injured limb or extremity of a patient in an emergency, combat, or pediatric situation comprising dispensing a foam of the present subject matter directly on the injured limb or extremity. A kit is also provided for stabilizing an injured limb or extremity comprising a dispenser comprising a foamable composition of the present subject matter. A spine board and a method for making the same comprising applying a foam of the present subject matter to the back of the patient and then contacting the foam with a board or flat surface before the foam sets. The present subject matter also relates to situ preparation and application of a compression bandage on an injured patient in an emergency or combat situation comprising applying a rigid foam of the present subject matter.

BRIEF DESCRIPTION OF THE DRAWINGS

FIG. 1B is a photograph of the case in FIG. 1A after the arm is removed from the cast. This example used the two-component quick-curing Spray Polyurethane Foam (SPF) sold under the trade name FROTH-PAK (Dow Chemical Corporation).

FIG. 2A shows the assembled kit. FIG. 2B shows packages of dry antibiotic, dry hemostatic agent, and a medical dressing for dressing open wounds. In this example of the kit, the packages may be placed under one or more end caps or attached to the can. Also in this example, a second detachable cap is provided having one open end and the other end of the cap is open and fitted with a detachable cover.

FIGS. 3A (top view) and 3B (side view) schematically show an example of a rigid foam cast of the present subject matter on an injured extremity having an open wound and comprising an open-ended walled-form with an optional detachable cover. The walled form is placed over the wound area before the rigid foam cast is sprayed on the injured extremity so that the wound can remain open to observation or access after the foam cast is dispensed to stabilize the injured limb or extremity.

DETAILED DESCRIPTION

The present subject matter relates to orthopedic splinting materials and methods for stabilizing an injured limb or extremity of a human or animal comprising applying a foam to the limb or extremity and allowing the foam set to sufficient rigidity. The currently known techniques for casting or splinting a human fracture have not changed much throughout the course of time. The mainstay is a large heavy splint made from either plaster-of-Paris, fiberglass, or in some new concepts polyurethane. Some of these materials and techniques have become commonplace and remain the standard treatment, but there have been many disadvantages to using these materials and techniques.

Plaster-of-Paris splints are typically very heavy and bulky for the patient. They also generally require several steps for application, and are not practical for application in most combat or emergency situations. The area to be splinted must be wrapped with web roll, which is simple cotton padding. The web roll is critical to get smooth so as not to create pressure sores. The plaster is then dipped into water, an essential step to activate the plaster, then the plaster is wrapped around the area circumferentially. The activated plaster initiates an exothermic chemical reaction, meaning heat is released from the plaster, which must be monitored so as to not burn the patient. As the area is drying, which takes several minutes, the plaster must be molded to ensure it does not simply fall off the extremity. Plaster casts are easily damaged by water, urine, and feces because the cotton web roll acts as a sponge and absorbs any and all fluids holding them on the skin causing irritation and break down. This damage forces the patient to return for another cast and more expense, inconvenience, and discomfort. This is particularly a problem in pediatrics due to patient compliance, and the activities they partake in. These casts are also heavy and bulky, even though they have a very low strength to weight ratio, thus the weight is not the patient's benefit. Plaster also has no expandability, which makes swelling a very dangerous problem for the patient and a concern for the orthopedic surgeon. Evaluating a patient with plaster is also difficult because plaster has poor radiolucence, obscuring the surgeon's view of the fracture site. Similarly, if the patient has other wounds on the injured extremity (such as cuts, sutures, open wounds, etc.) and they are covered by the plaster cast, then these may be obscured or require other special procedures.

Fiberglass splints are used and applied in much the same way as that of plaster. They require cotton web roll pre-wrap and extreme caution during application so as not to create areas of pressure. Fiberglass also requires water to activate the chemical reaction; this reaction is also exothermic and must be monitored for burns. Fiberglass is also known for drying with very sharp edges that must be padded and constantly monitored for skin irritation and break down. Skin break down may require frequent trips to the clinic for cast adjustment, costing time and money.

Lastly, these traditionally splints are used in the pediatric patient population which has additional concerns and consideration for the patient and the surgeon. One of the most problematic aspects is getting a pediatric patient to hold still long enough for the surgeon to apply and mold the cast or splint. This is usually overcome by sedating the patient, and often this requires a trip to the operating room to provide adequate respiratory and cardiac monitoring. This extra step not only puts the child at risk of a reaction to the anesthesia but can also cost thousands of dollars. Another common problem with this population is soiling of the cast or splint. For example, a spica cast is placed around the hips and down each leg, where soiling is common and there is concern that the cotton web-roll under the cast will absorb urine and feces and hold it on the skin causing skin break down and multiple trips to the operating rooms for cast changes. A cast that does not absorb liquids and is easily wiped clean would cut huge amounts of cost and possible injury to the patient. Another advantage would be a cast that cures much faster thus lessening the time of anesthesia.

The casting and splinting techniques described thus far are most often used in a clinic setting and not an acute or emergency situation. The modern paramedic has very few options when treating a fracture in the field, due to the portability, size and time most casting techniques require. One such technique is inflatable splints made of plastic; these devices are slipped over the extremity and then inflated, thus providing minimal immobilization and forcing the paramedic to move the extremity, and the extremity is forced to take the shape of the air splint. Another common method used is the S.A.M. (Structural Aluminum Malleable) splint. This is a flexible metal covered in foam, which is wrapped around the extremity to provide immobilization. This product also requires the paramedic to move the extremity and wrap it in a circumferential manner, and the splint being made of metal, the mold and conformability is limited often requiring an elastic wrap to be placed around it. Both of these methods require the paramedic to manipulate the extremity causing pain, and more importantly possible neurovascular injury. As bone fractures, sharp edges are often produced that if moved can easily cut a delicate nerve or artery causing unnecessary and devastating complications. These techniques also provide very little if any means of controlling bleeding, thus leaving the paramedic to make a decision to either control bleeding or immobilize the fracture. The ideal splint could provide both immobilization and hemodynamic control.

Solid foam compositions, including polyurethane foam compositions have been described previously in the medical field for use as implants and padding. Generally, such foams are inert and do not react with biological components in the human body and provides little risk of anaphylaxis. Polyurethane foams have also been previously described for use in preparing casts or splints. However, all of these methods use polyurethane in a traditional manner, activating it with water and wrapping the extremity or filling a mold. Generally, the polyurethane foams described in the cast/splint art produce excessive exothermic heat that causes patient discomfort, pain, and/or burns on uncovered skin. Also, generally, such polyurethane foams require at least several minutes before the foam will set to sufficient rigidity required to stabilize the injured extremity or limb. U.S. Pat. No. 4,952,447 describes a polyurethane tape-like material that must be activated with water and then must be wrapped circumferentially over a prewrap. U.S. Pat. No. 4,309,990 describes spraying foam on a bandage strip, applying an under garment, and wrapping the extremity with the foam bandage strips over the undergarment. U.S. Pat. No. 6,695,801 describes a polyurethane foam between two layers of material that must expand and form to fit, this takes 12 minutes and has poor surface contact. U.S. Pat. Nos. 2,947,307 and 3,301,252 describe polyurethane foam splints that require a cloth prewrap to protect from excessive exothermic reaction heat, also the foams described require several minutes to set to sufficient rigidity.

The foam splints and methods of the present subject matter overcome many or all of the disadvantages of using previously known foam splint materials and methods of applying them.

As used herein the terms "foam" and "rigid foam" refer to a three-dimensional porous material having a reticulated configuration in cross section and which is pliable and comfortable before it sets, and which after it sets is sufficiently rigid to stabilize a broken or injured limb or extremity of a human or animal. The terms "rigid" or "sufficient rigidity" as used herein refer to a structure that is sufficiently rigid to stabilize a broken or injured limb or extremity of a human or animal. The term "semi-rigid" as used herein refers to a foam that is substantially rigid or rigid to at least some degree or rigid in at least some parts, and may provide sufficiently rigidity to stabilize a broken or injured limb or extremity of a human or animal in some embodiments. The term "semi rigid" as used herein also refers to a foam a structure that is substantially rigid or rigid to at least some degree r rigid in at least some parts, and is used as to describe some insulation foams in the construction trades. In general, foams of the present subject matter are quick-setting foams. In some embodiments, the foams set to sufficient rigidity in less than 5 minutes, such as, for example, less than 4 minutes, less than 3 minutes, less than 2 minutes, less than 90 seconds, less than 60 seconds, or less than 30 seconds. The term "set" and "setting" as used herein refers to the foam achieving a sufficient rigidity after the foamable composition is generated and/or applied.

Quick-setting foams generally undergo an exothermic reaction (release of heat) during the formation and/or setting of the foam. In some foams of the present subject matter, heat is generated for less than 30 seconds as the foam forms and then the generated heat begins dissipating once the foam sets. In some embodiments, the temperature generated by the foam reaches a peak temperature in less than 30 seconds. In one embodiment, the foam of the present subject matter does not produce an amount of heat release that is uncomfortable, painful, burning, or a combination thereof, including when applied directly on the skin. Polyurethane foams previously used in the art of forming a splint or cast have produced significant amount of heat release that is uncomfortable, painful, or burning, and requires use of prewraps or other skin-covering to remove or minimize these adverse effects. In one embodiment, the foam of the present subject matter will generate an amount of heat release that is not uncomfortable, painful, or burning when applied directly to skin wherein the average peak temperature of the foam measured at the skin is selected from the group consisting of: 110° F., less than 110° F., 108° F., less than 108° F., 106° F., less than 106° F., 105° F., less than 105° F., 104° F., less than 104° F., 103° F., less than 103° F., 102° F., less than 102° F., 101° F., less than 101° F., 100° F., and less than 100° F.

According to one embodiment, the foam of the present subject matter is used as a splinting or casting device for bone fractures, and may be applied directly on to the skin of the injured extremity creating a perfectly contoured and pressure distributing fixation. Applying a foam of the present subject matter directly on the skin advantageously eliminated the need for any and all prewraps, such as circumferential wraps. Allowing the splint to be applied directly onto the skin eliminates the need to use absorbent cotton cast padding that harbors moisture and bacteria, which commonly occurs with the use of conventional splints and casts. Therapeutic agents, such as, for example, antibiotics, analgesics, and/or hemostatic agents, can optionally be added to the foamable composition, thus adding another line of defense to preventing infection, providing comfort, and/or stopping bleeding.

Foams and methods of the present subject matter can be advantageously applied while the wound remains in situ (position of fracture) in the field even before the patient is extracted from the scene of the injury. Thus, the present subject matter advantageously allows the injury to be stabilized without manipulation, which is a significant improvement upon prior art methods and casts which require the injury to be wrapped circumferentially with an absorbent dressing and which results in the injury being subjected to manipulation and movement. Keeping fractures in their in situ position until the patient is transported to a medical facility generally decreases the likelihood of secondary tissue injuries, bleeding, and infection associated with moving and manipulating a fractured extremity before the injury is treated. Accordingly, the present subject matter may also reduce multiple examinations of the open fracture which has been shown to increase the rate of infection; the fracture can be left in place until the treating physician arrives.

Advantageously, the simplicity of using the methods of the present subject matter permit both trained emergency medical personnel and minimally-trained personnel (e.g. non-medical personnel, combat soldiers, etc) to successfully practice the methods without significant difficulty.

In one embodiment, the foams of the present subject matter may provide one or more advantageous features selected from the group consisting of: the foam splint or cast can be applied quickly; the foam splint or cast can be applied with minimal technical training; the foam splint or cast can be applied in the field environment, such as under combat or emergency response conditions; and the foam splint or cast can be applied on the extremity in its observed position to stabilize it during extraction. Foams of the present subject matter are generally very light weight even after it hardens, while its strength is not compromised creating a very favorable weight to strength ratio. The load capacity (strength) can be easily manipulated allowing the physician many options to meet the needs of a very diverse patient population. In some embodiments, foams of the present subject matter are radiolucent (X-rays can be taken through it) which allows the surgeon or clinician to easily assess the bone using radiographs. Additionally, numerous embodiments of foams of the present subject matter are generally impervious to water and may chemicals, and thus do not absorb urine, sweat, or other bodily fluids that often contaminate traditional casts. A further benefit is setting time, foams of the present subject matter set to a rigidity to stabilize an injured limb or extremity quickly. Foams of the present subject matter also cure to sufficient dryness and may embodiments are tack-free and at full strength in less than 5 minutes and are tack-free and at sufficient rigidity and strength, making it advantageous in emergencies, military combat, and pediatric splinting. In one embodiment, the foam is sufficiently tack-free and at full strength in less than 60 seconds.

In some embodiments, the foam sets as an open-cell foam. The term "open cell" as used herein refers to a foam wherein the majority of adjoining cells are in open communication with each other, such that interconnected cells form spaces, chambers, and channels larger than individual foam cells. In some embodiments, open cell foam structure forms during the setting process where individual foam cells at least partially open their wall structure with adjoining cells and then set as a rigid foam. In some embodiments, use of an open cell foam advantageously provides sufficient rigid support of the limb or extremity while simultaneously providing improved airflow to the skin which maximizes comfort and helps to decrease sweating, trapping of contaminants against the skin, and formation of sores, problems common in traditional casts and wraps.

Foams of the present subject matter may include any synthetic-based or natural based foam formulation that can provide sufficient rigidity and also optionally provide one or more of the uses or features disclosed herein. One embodiment of the present subject matter includes applying a foam that provides quick and effective immobilization of fractures. Non-limiting examples of foam formulations that may be useful for the present subject matter, having one or more of the features described herein, include polyurethane foams and soy-based foams. There term "polyurethane foam" as used herein refers to foam of the present subject matter obtained from the polyurethane that is the reaction product between a polyisocanate and at least one polymer polyol. The polyisocyanates and polyols of polyurethane foams of the present subject matter may be derived from synthetic sources and/or natural sources, such as purified and/or synthesized from petroleum or agricultural products (such as soy). In one embodiment, the polyurethane foam of the present subject matter may be based largely on soy beans, such as American-grown soy bean extract, improving safety and environmental concerns. In one embodiment, polyurethane foams are formulated as a two-component foam.

The term "two-component foam" as used herein refers to a foam that is produced from the combination of two precursor compositions which must be combined in order to activate the foaming process. A two-component polyurethane foam composition is one non-limiting example of the two-component foam compositions of the present subject matter. In one embodiment, a two-component foam provides one component in one pressurized container, typically the "A" container (i.e. polymeric isocyanate, fluorocarbons, etc.) while a resin is supplied in a second pressurized container, typically the "B" container (i.e. polyols, epoxy, polyester, latex, catalyst, flame retardants, etc.)

Spray polyurethane foam (SPF) is a product that is commonly used in building and manufacturing as semi-rigid foam insulation. In some embodiments, SPF formulation comprises a two-component quick-cure foam formulation. In one combination, the SPF comprises the two components of isocyanates and polyols sprayed as a liquid on a surface and within seconds expands and dries rigid or semi-rigid depending upon the formulation selected. In one embodiment, the SPF formulation is a commercially available polyurethane two-component quick-setting foam known by the trade name FROTH-PAK, in package size named FROTH-PAK-12 for 12 board feet of foam, and is manufactured by Dow Chemical (Midland, Mich.). Other package sizes of FROTH-PAK foam are commercially available for differing uses and often with different nozzles depending upon the application, and are useful as a foam of the present subject matter. FROTH-PAK-12 foam sets to sufficient rigidity with no-tackiness in less than 60 seconds, and in less than about 30 seconds. The commercially available series of FROTH-PAK foams generally provide a foam density ranging from about 1.7 to about 3.4 pounds per cubic foot. FROTH-PAK-12 provides a foam density ranging from about 1.7 pounds per cubic foot to 1.9 pounds of cubic foot.

It is noted that the FROTH-PAK series of foam provides a foam that sets to sufficient rigidity in less than 60 seconds, and does not produce an amount of heat release that is painful or uncomfortable on the skin of the human or animal. Commercially available FROTH-PAK-12 is so-named because it provides 12 board feet of foam. In one embodiment, the FROTH-PAK foam is formulated in a two-component can to provide a volume of foam that differs from the volume of foam that is currently commercially available. For example, FROTH-PAK foam may be formulated in a two-component can to provide 1,2,3,4,5,6,7,8,9 or 10 board feet of foam.

In one embodiment, the SPF polyol component formulation comprises: (1) Polyols Mixture 30-60%; (2) Diethylene Glycol CAS#111-46-4-6 1-5%; (3) Triethyl Phosphate CAS#78-40-0 1-5%; (4) Flame Retardants Mixture 5-10%; (5) 1,1,1,3,3-Pentafluoropropane CAS#460-73-1 713%; and (6) 1,1,1,2-Tetrafluoroethane CAS#811-97-2 10-30%. Data from FROTH-PAK Polyol component blend, MSDS (rev. Mar. 10, 2006), incorporated herein by reference in its entirety.

In one embodiment, the SPF isocyanate component formulation comprises: (1) Methyleneniphenyl, diisocyanate, homopolymer, about 40.0-60.0%, CAS#39310-05-9, EC# Polymer; (2) 4,4'-Methylenediphenyl diisocyante diphenylmethane-4,4'-diisocyanate (MDI), about 40.0-60.0%, Classified Xn: R20, Xi:R36/37/38, R42/43, CAS#101-68-8-202-966-0; and (3) 1,1,1,2-Tetrafluoroethane, about 5.0-10.0%, CAS#811-97-2, EC#212-377-0. Data from, FROTH-PAK Isocyanate component, MSDS (Rev. Oct. 7, 2006), incorporated herein by reference in its entirety.

In one embodiment, the FROTH-PAK spray foam formulation can provide the following features in the final foam product: Tack-free Time, <60 seconds, Tensile Strength, ASTM D1623, psi (kPa), parallel about 40.1 (276.4); Shear Strength, ASTM C273, psi (kPa), parallel about 23.9 (164.8); Flexural Strength, ASTM C203, psi (kPa), min about 23 (158.6); Compressive Strength, ASTM D1621, psi (kPa), min about 22 (151.7); Apparent Core Density, ASTM D1622, lb/ft3 (kg/m3) about 1.70 (27.2); Water Absorption, ASTM D2842, % by volume max, about 2.5; Water Vapor Permeance, ASTM E96, perm (ng/Pa*s*m2), max. about 3.0 (4.38).

The load capacity of some two-component polyurethane foams, including FROTH-PAK foams, may be changed by changing the amount or type of blowing agent. That is, changing the amount and/or type of blowing agent can vary foam density to achieve different compressive strengths. FROTH-PAK foams generally comprise a hydrofluorocarbon in the blowing agent composition. Foamable compositions may also be optionally premixed with water in some embodiments. Water can be optionally included in the blowing agent composition of SPF's of the present subject matter. Generally, decreasing the amount of water used in the SPF blowing agent results in foams having increased rigidity, and increased elastic modulus. The expansion of the foam is also able to be adjusted thus following even thinner equally strong casts to be applied. The nozzle shape also determines the physical features of the sprayed foam in some embodiments. In one embodiment, a fan-spray shaped nozzle is used to provide fast delivery and coverage of an injured limb or extremity. The manipulation of load capacity of a foam may result in foams suitable for different uses. For example, a foam can be made hard enough to actually add structural strength to buildings or soft enough to insulate flexible hoses. In one embodiment for larger adults, a more dense formula could be used as compared to an embodiment for a smaller pediatric patient which might be less dense. In addition to density, the strength of a rigid polyurethane foam may also be designed by selecting factors such as catalyst, surfactant, type of mixing, and the type and proportions of the foaming system: base polyol and isocyanate. Also, besides its strength, polyurethane foam that has set is also impervious to water and resists absorption of other chemicals, an advantage for preserving the durability and comfort of casts and splints.

The term "applied" as used herein refers to placing the foamable composition or foam on the intended site of use, such as, for example, on an injured limb or extremity, on an injured back, etc. In some embodiments, the foamable composition is activated to begin the formation of foam and then the foamable compositions and/or foam is applied to the site of intended use. In one embodiment, a two-component foamable composition is mixed to initiate the formation of foam and then the activated foamable composition is manually applied to the site of use. In another embodiment, a two-component foamable composition is mixed to initiate the formation of foam and then the activated foamable composition is applied by spraying the composition on the site of use. Any suitable propellant may be used to spray the foam formulation, non-limiting examples include physical volumetric pressure and chemical propellants, such as hydrocarbons and fluorohydrocarbons. In a further embodiment, a foam of the present subject matter is formulated as a spray foam composition premixed with one or more fluorohydrocarbon propellants. In one embodiment of a two-component spray foam composition, the two components in separate containers are mixed together by channeling both components through a single applicator nozzle, wherein the two components mix in or near the nozzle to activate the formation of foam and simultaneously the applicator nozzle is used to apply the foam. In another embodiment, the two-components of a foam of the present subject matter are in two separate cans; the two separate cans are then further attached to one another or are enclosed in a single can, container, or package; and the two-component cans are individually connected to a single applicator or nozzle where the two-components may be mixed at the time of application at or near the applicator or nozzle.

Generally, foam from a two-component SPF system is applied by mixing both components to activate the foaming reaction, and then applying the mixture to the selected location where foam is desired. In one embodiment, the components are manually mixed and the foam is manually applied. In another embodiment, the two components are mixed by spraying the components to form the foam where it is desired. The two components may be mixed by simultaneously directing both components through a single spray nozzle.

In one embodiment, the foam of the present subject matter is applied quickly by spraying and without calculating the volume or quantity of each component.

The term "patient" as used herein refers to any human or animal that may benefit from the use of any of the foam embodiments described herein. In some embodiments, a patient is a human or animal that requires a cast or splint to stabilize an injured limb or extremity, or requires spine board to immobilize the spine or head, or requires a compression bandage to stop or slow bleeding. Some non-limiting examples of a patient include adults, children, infants, domesticated animals, wild animals, pets, zoo animals, farm animals, dog, cats, birds, horses, cattle, primates, and reptiles. The term "skin" as used herein refers to the keratinized epidermis, mucosal epithelia, and epidermis covered partially or totally by hair or fur of a human or animal.

The term "injured limb or extremity" as used herein refers to a body part that is injured and that may require immobilization to minimize pain or discomfort of the injury, and/or to promote healing of the injury, and/or to promote effective therapy for the injury. Non-limiting examples of limbs or extremities include arms, shoulders, elbows, wrists, hands, fingers, legs, hips, knees, ankles, toes, neck, and back. Non-limiting examples of injuries include broken bones, damaged tissue, stretched or torn ligaments and tendons, surgical trauma, and surgical reconstruction. In one embodiment, the foams of the present subject matter are useful for preparing post-surgical splints/casts for any orthopedic-related surgery, including, for example, an open reduction internal fixation (ORIF) procedure. The term "open wound" as used herein refers to an injury characterized by trauma to the skin involving an opening or cut in the skin.

The term "therapeutic agent" as used herein refers to an agent that promotes, induces, increases, or accelerates wound or injury healing or initiates, accelerates or improves tissue growth, decreases or prevents growth undesirable bacteria or fungi, or reduced or eliminates the sensation of pain in the patient. Suitable therapeutic agents include, but are not limited to, antibiotic agents, hemostatic agents, and anesthetic agents. In one embodiment, the therapeutic agent is applied directly to a wound on the animal or patient before the foam is applied. In another embodiment, at least one therapeutic agent may be provided in a kit for oral-or-injectable administration to the patient. In one embodiment, the therapeutic agent is a dry and/or granular formulation. In general, biomedical studies have shown that the sooner a wound is treated with antibiotics then the infection rate decreases. In one embodiment, the antibiotic gentamycin, tobramycin, vancomycin, or a combination thereof is added to the foamable composition before it is applied, and both antibiotics have been shown to remain stable after being exposed to a moderate exothermic environment, such as the mild to moderate exothermic environment that may be generated by the foams of the present subject matter.

Non-limiting examples of antibiotic agents include chemical agents; Aminoglycosides; Ansamycins; Carbacephems; Carbapenems; Cephalosporins; Glycopeptides; Lincosamides; Macrolides; Monobactams; Nitrofurans; Penicillins; Polypeptides; Quinolones; Sulfibanudes; Tetracyclines; Anti-mycobacterials; and other Antibiotics. Non-limiting examples of chemical agents include iodine, peroxide, and mercurochrome. Non-limiting examples of Aminoglycosides include Amikacin, Gentamicin, Kanamycin, Neomycin, Netilmicin, Tobramycin, and Paromomycin. Non-limiting examples of Ansamycins include Geldanamycin and Herbimycin. Non-limiting examples of Carbacephems include Loracarbef. Non-limiting examples of Carbapenems include Ertapenem, Doripenem, Imipenem/Cilastatin, and Meropenem. Non-limiting examples of Cephalosporins include Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperzone, Cefotaxime, Cefpodoxime, Ceftazidime, Ceftibuten, Ceftizoxime, Ceftriaxone, Cefepime, and Ceftobiprole. Non-limiting examples of Glycopeptides include Teicoplanin, Vancomycin, and Telavancin. Non-limiting examples of Lincosamides include Clindamycin and Lincomycin. Non-limiting examples of Macrolides include Azithromycin, Clarithromycin, Dirtithrymycin, Erythomycin, Roxithromycin, Troleandomycin, Telithromycin, and Spectinomycin. Non-limiting examples of Monobactams include Aztreonam. Non-limiting examples of Nitrofurans include Furazolidone and Nitrofurantoin. Non-limiting examples of Penicillins include Amoxicillin, Ampicillin, Azlocillin, Carbenicillin, Cloxacillin, Dicloxacillin, Flucolxacillin, Mezlocillin, Methicillin, Nafcillin, Oxacillin, Penicillin G, Penicillin V, Piperacillin, Temocillin, and Ticarcillin. Polypeptides include Bacitracin, Colistin, and Polymyxin B. Non-limiting examples of Quinolones include Ciprofloxacin, Enocacin, Gatifloxacin, Levofloxacin, Moxifloxacin, Nalidixic acid, Norfloxacin, Ofloxacin, Trovafloxacin, Grepafloxacin, Sparfloxacin, and Temafloxacin. Non-limiting examples of Sulfanomides include Mafenide, Sulfonamidochrysoidine, Sulfacetamide, Sulfasalazine, Sulfsoxazole, Trimethoprim, and Trimethoprim-Sulfamethaxazole. Non-limiting examples of Tetracyclinees include Demeclocycline, Doxycycline, Minocycline, Oxytetracycline, and Tetracycline. Non-limiting examples of Anti-mycobacterials include Clofazimine, Dapsone, Capreomycin, Cycloserine, Ethambutol, Ethionamide, Isoniazid, Pyrazinamide, Rifampicin, Rifabutin, Rifapentine, and Strepthomycin. Non-limiting examples of other Antibiotics include Arsphenamine, Chloramphenicol, Fosfomycin, Fusidic acid, Linezolid, Metronidazole, Mupirocin, Platensimycin, Quinupristin/Dalfopristin, Rifaximin, Thiamphenicol, and Tinidazole).

One non-limiting example of a hemostatic agent is QUIK-CLOT. Non-limiting examples of anesthetic agents include lidocaine, prilocaine, bupivicaine, levobupivacaine, ropivacaine, mepivacaine, dibucaine, procaine, amethocaine, and combinations thereof.

The term "medical dressing for open wounds" as used herein refers to a medical dressing for covering and protecting open wounds from contamination and/or environmental elements. In one embodiment, the medical dressing for open wounds is breathable and transparent, such as, for example, TEGADERM. The term "open wound" as used herein refers to an area of skin that has been open by injury or trauma, such as, for example, bullet and shrapnel wounds, cuts, burns, sutured wounds, severe skin disease, severe tissue disease, and surgical trauma. In one kit embodiment, a medical dressing such as TEGADERM, is provided in a package accompanying the can, such as, attached to the can or under the cap on the can.

The term "cleaning irrigant" as used herein refers to a physiologically compatible liquid useful for irrigating and cleaning a wound area to remove foreign debris. Non-limiting examples of cleaning irrigants include, saline, water, blood plasma, liquids containing one or more an antibiotic compounds (such as gentamycin, vancomycin, tobrimycin), and combinations thereof.

The term "dye or coloring agent" as used herein refers to a synthetic or natural chemical or chemical composition that may be added to the foamable formulation to cause the final rigid foam to have a selected color. Non-limiting examples of colors that dye or coloring agent may provide include, for example, green, sand, black, blue, pink, red, orange, yellow, and metallic colors. The color of the foam may be changed for a variety of reasons including, for example, providing camouflage for combat situations; providing identification for emergency situations; providing event information to assist clinical diagnosis; and providing color preferences for patients, including children and parents of pediatric patients.

In one embodiment, a cast for stabilizing an injured limb or extremity of a human or animal is provided comprising a foam applied directly to the human or animal without requiring a prewrap and allowed to set into a sufficiently cast. In one embodiment, a cast is provided comprising a foam sprayed directly onto the skin of the limb or extremity and allowed to set. In another embodiment, a cast is provided comprising a foam sprayed directly onto the skin and the foam does not produce an amount of heat release that is painful or uncomfortable on the skin of the human or animal. In yet another embodiment, the foam is a polyurethane foam, such as, for example, a two-component quick-cure polyurethane foam. Also, for example, the polyurethane foam of the present subject matter may be a polyurethane foam that is not activated by water, and/or a polyurethane foam that does not produce an amount of heat release upon activation that is painful or uncomfortable on the skin of the human or animal. In a particular embodiment, the foam is FROTH-PAK foam, a two-component quick-cure polyurethane foam, commercially available and produced by Dow Chemical Company. In another embodiment, the foam is soy-based foam. In several embodiments, the foam is an open-cell foam. In some embodiment, foams of the present subject matter set to sufficient rigidity in less than 30 seconds.

The present subject matter also provides a method for stabilizing an injured limb or extremity of a human or animal comprising spraying a foam of the present subject matter on the injured limb or extremity of a human or animal, wherein the foam does not produce an amount of heat release that is painful or uncomfortable to the human or animal; and allowing the foam to harden into a cast having sufficient rigidity in less than 60 seconds.

The rigid foam cast or splint may be readily removed by conventional methods, include cutting the cast from the body using a knife, saw, laser, heating element, chemical degradation, or other method. In one embodiment, if the foam is applied directly to the skin, a thin layer of lubricating or insulating composition or emollient may be optionally topically applied to the skin before the foam is applied to increase the ease of removing the cast or splint from the injured limb or extremity.

In one embodiment, the cast is prepared in a combat or emergency situation at or near the geographic location where the injury occurred. In some embodiments, the injured limb or extremity comprises broken bone, damaged or missing tissue, cuts, sutures, bullet or shrapnel wounds, or other open wounds. In another embodiment, the foam cast also shows or stops bleeding from a cut or wound on the injured limb or extremity. Foams of the present subject matter may further comprise an active therapeutic agent, such as, for example, an antibiotic or hemostatic agent. Foams of the present subject matter may further comprise a dye or coloring agent, such as, for example, a dye to color the cast in a combat camouflage color, such as green, sand, black, etc. In another embodiment, a method of preparing a cast further comprises irrigating a wound area on the injured limb or extremity with a saline solution to remove contaminants or foreign debris before applying the foam. In yet another embodiment, a method of preparing a cast further comprises applying at least one antibiotic agent to a wound area on the injured limb or extremity before applying the foam, such as, for example, at least one antibiotic agent is selected from the group consisting of Tobramycin, Vancomycin, Gentamycin, Cefazolin, or a combination thereof. In still another embodiment, a method of preparing a cast further comprises applying the foam. In a further embodiment, a method of preparing a cast further comprises applying at least one anticoagulant to a wound area on the injured limb or extremity before applying the foam. In a further embodiment, a method of preparing a cast further comprises applying at least one medical dressing for open wounds to a wound area on the injured limb or extremity before applying the foam.

In a further embodiment, a method of preparing a cast further comprises obtaining a walled-form with walls enclosing an empty interior space and having one open end and the other end is either transparent or open and fitted with an optional detachable cover, wherein the width of the walled-form is less than the width of the injured limb or extremity; placing the open end of the walled-form against the limb or extremity and around a selected wound area on the injured limb or extremity before dispensing the foam on the injured limb or extremity; dispensing the foam around the outside of the walled-form and on the injured limb or extremity so that the walled-form prevents foam from covering the wound area; and forming an observation area to observe the wound inside the walled-form after the foam is dispensed to stabilize the injured limb or extremity. In one embodiment, the walled-form also functions as a cap or end piece that is attached to a foam dispenser, such as a spray can of foam.

In one embodiment, the subject matter of the present subject matter also provides a one-step method is provided for stabilizing an injured limb or extremity of a human or animal in an emergency or combat situation comprising dispensing a foam directly on the skin or clothing of the injured limb or extremity of the human or animal, wherein the foam does not produce an amount of heat release that is painful or uncomfortable on the skin of the human or animal, wherein the foam hardens into a cast having sufficient rigidity in less than 60 seconds, such as, for example, in less than 30 seconds.

In another embodiment, the subject matter of the present subject matter also provides a kit for stabilizing an injured limb or extremity of a human or animal in an emergency or combat situation comprising a dispenser comprising a foamable composition of the present subject matter, wherein the foam sets to sufficient rigidity in less than 60 seconds after dispensing the foam on the injured limb or extremity. In one embodiment, the foam in the kit does not produce an amount of heat release that is painful or uncomfortable on the skin of the human or animal. In a further embodiment, the kit further comprises one or more components to be applied to the injured limb or extremity before the foam is dispensed on the injured limb or extremity selected from the group consisting of at least one package comprising a cleaning irrigant; at least one package comprising a hemostatic agent; at least one package comprising an antibiotic agent; at least one agent comprising an anesthetic agent; at least one package comprising a medical dressing for open wounds; and combination thereof. In one embodiment, the kit further comprises one or more components to be applied to the injured limb or extremity before the foam is dispensed on the injured limb or extremity selected from the group consisting of at least one package or dispenser comprising saline irrigant; at least one package comprising QUIK-CLOT hemostatic agent; at least one package comprising an antibiotic agent selected from the group consisting of Tobramycin, Vancomycin Cefazolin, or a combination thereof; at least one package comprising TEGADERM wound dressing for dressing open wounds; and combinations thereof. In one embodiment, the kit comprises a first dispenser comprising a foamable composition of the present subject matter; a second dispenser comprising a cleaning irrigant; at least one package comprising a hemostatic agent; at least one package comprising an antibiotic agent; at least one package comprising a medical dressing for open wounds; and an open-walled form for creating an observation area in the cast.

In one embodiment, the first dispenser and second dispenser are both integrated into a single can with a first nozzle or dispenser at one end for spraying the foam from a first chamber(s) of the can, and a second nozzle or dispenser at the other end for applying a cleaning irrigant contained in another chamber of the can. In another embodiment, the kit further comprises a timing device to be affixed to the patient or cast which may be activated at the time the cast is applied to provide information to the medical care provider of time of injury. In a further embodiment, each dispenser end, caps on the ends of the dispenser, and/or kit component are color-coded, pattern-coded, number-coded, and/or word-coded to provide one or more indicators of which end and/or component should be opened and applied first, and which should be opened and applied second, etc. In a yet another embodiment, written instructions for using the kit and/or one or more of its components are included in the kit, such as, for example, affixed to the outside of the dispenser, written on individual component packages, and/or as one or more separate documents. In many embodiments, the kit is lightweight, portable, and easily stored and transported by emergency personnel, in military combat packs, in private of public vehicles and transportation, and in first aid kits. The widespread availability and use of a kit of the present subject matter in society can significantly improve quality and speed of emergency and orthopedic healthcare of stabilizing and treating injuries and wounds while minimizing the pain and discomfort of the patient.

In yet another embodiment, the kit further comprises a walled-form (such as, for example, a detachable cap or end piece attached to the dispenser in the kit) having one open end and the other end is either transparent or open and fitted with a detachable cover, the cap or end piece can be placed around a selected wound area on the injured limb or extremity to prevent foam from covering the wound area so that it can remain open to observation after the foam is dispensed to stabilize the injured limb or extremity. The walled-form has sufficient structural integrity to maintain an open observation area in the cast on the injured limb or extremity, the observation area in the cast being free of foam after the foam is applied to the limb or extremity. In one embodiment, an open ended walled form is placed over the wound area before the rigid foam cast is spayed on the injured extremity. The walled-form may be made of any material having the sufficient structural integrity. Non-limiting examples walled-form materials include plastics, polymers, rubber, metals, artificial fiberts (such as fiberglass), natural fibers (such as paper or cardboard), recycled materials, and other materials. Open-ended walled-form with an optional detachable cover. The present subject matter also provides a cast, and a method of making a cast, having an open observation area in the cast on the injured limb or extremity for observing a wound on the limb or extremity. The observation area in the cast being free of foam after the foam is applied to the limb or extremity. In some embodiments, a cast having an observation area over a wound advantageously provides stabilization of an injured limb or extremity while simultaneously allowing the wound to remain open to observation or access so that medical care personnel can assess and/or treat the wound without removing the stabilizing cast.

Figure 4A:
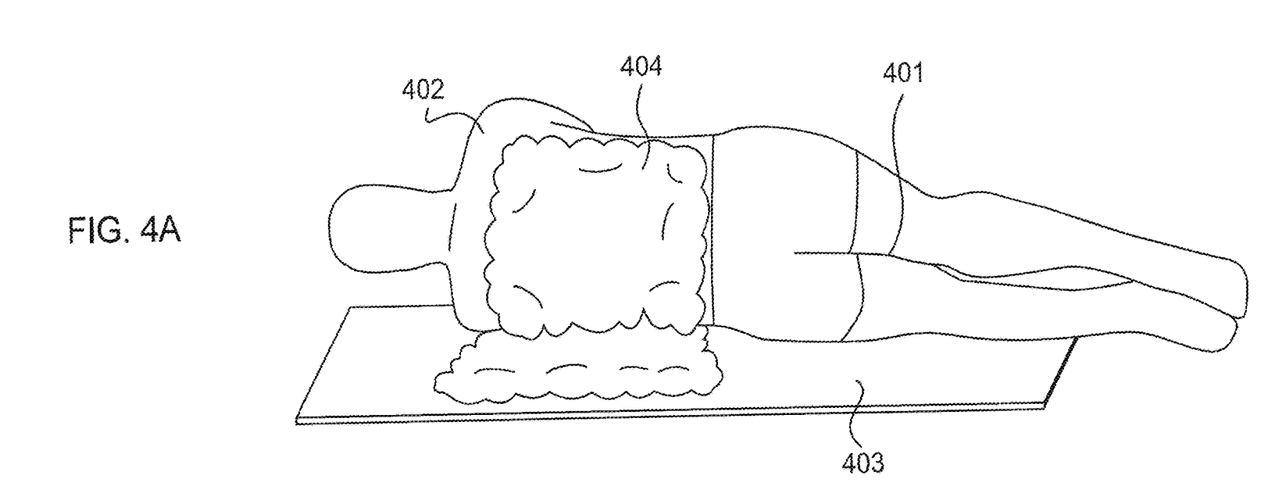
FIGS. 4A and 4B schematically show one embodiment of a spine board of the present subject matter and a method of preparing and placing the spine board on the patient.
Figure 4B:
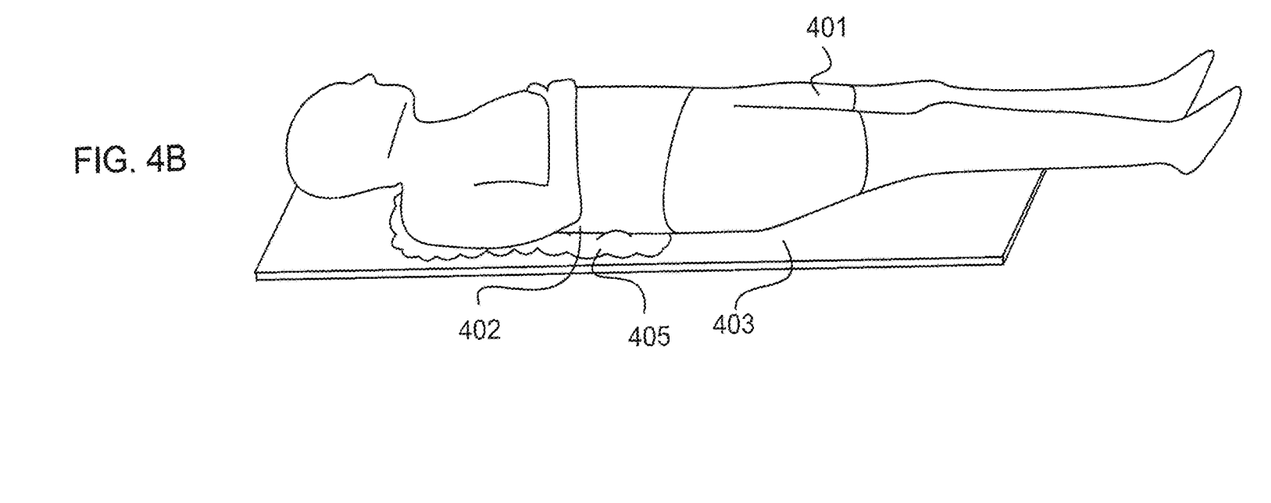

In a further embodiment, the subject matter of the present subject matter also provides a spine board for stabilizing an injured patient comprising a foam of the present subject matter applied onto the back of the patient and allowed to set while the foam on the patient's back in contacting a board or flat surface. In one embodiment, a foam of the present subject matter is sprayed directly on the skin or on the clothing of the patient, or on the board or flat surface, and the foam does not produce an amount of heat release that is painful or uncomfortable for the patient. FIGS. 4A and 4B show one example of the present spine board and a method for in situ manufacture and placement of a spine board for stabilizing an injured patient (401) comprising rolling the patient to at least partially raise the back (402) of the patient (401); placing a board or flat surface (403) under the back of the patient; dispensing a foam of the present subject matter (404) on the clothed or unclothed back (402) of the patient, on the surface of the board or flat surface (403), or a combination thereof; rolling the back (402) of the patient onto the board or flat surface (403) before the foam has set (404), wherein the foam does not produce an amount of heat release that is painful or uncomfortable to the patient; and allowing the foam to harden (405) into a spine board having sufficient rigidity in less than 60 seconds. In some embodiments, the spine board also comprises at least one restraint or strap for keeping the patient securely attached to the spine board. In another embodiment, the board or flat surface used to make the spine board has one or more holes or depressions, an uneven surface, a textured surface, or a combination thereof. The very nature of the foam also creates a very strong flotation device that could be applied to the spine as a buoyant spine board for water extractions.

In one embodiment, the subject matter of the present subject matter also provides a method for the situ preparation and application of a compression bandage on an injured patient in an emergency or combat situation comprising applying a foam of the present subject matter on the injured patient and covering the wound requiring a compression bandage, wherein the foam does not produce an amount of heat release that is painful or uncomfortable on the skin of the human or animal; and allowing the foam to harden in less than 60 seconds to a rigidity sufficient to stop or slow the flow of blood. In some embodiments, foams of the present subject matter, including SPF, sprayed circumferentially around an entire extremity can slow or stop bleeding from an open wound due in-part to the fact that the foam does not absorb fluids, and thereby keeps bleeding compressed at the site of the open wounds. Accordingly, the present subject matter may be useful for preparing compression bandages.

The subject matter of the present subject matter also provides a method for in situ preparation of a compression pad for minimizing the occurrence of pressure sores in the feet of diabetic humans. Pressure sores may occur in variety of circumstances. Non-limiting examples include bed-ridden patients, surgical patients, diabetic, feet, repetitive work motions, bony protuberances, carrying large packs of burdens, saddle sores, and pack sores. In situ preparation and application of a foam of the present subject matter on the area on the body, wherein the foam takes on the precise contours of the body, and thereby creates an even stress load distribution which minimizes the likelihood of pressure sores developing on the body area having the foam padding of the present subject matter. In one embodiment, the patient is suffering from bed sores, and the patient is lowered to the mattress to position the body on the in situ made foam padding. The foam padding may be optionally re-used if it can be precisely places in the same body position. In another embodiment, a patient's body is positioned for surgery, and then the body location prone to sores is slightly lifted and SPF is sprayed onto the body location and the patient carefully lowered to the surgical mat so that the foam creates an even stress load distribution which minimizes the likelihood of pressure sores developing on the padded body location. In another embodiment, the skin of a horse, or beast of burden, to be located under a saddle or pack is sprayed with a layer of SPF and the saddle of pack is immediately placed over the foam and the saddle or pack is compressed to create a pad that follows the contours of the body.

The following are non-limiting examples of the subject matter described herein.

Example 1

FROTH-PAK-12 (Dow Chemical Corporation) was obtained from a construction supply store. The product contained one pressurized can of isocyanate formulation and another pressurized can of polyol blends. Both cans were connected by tubes to a single spray handle with a single nozzle. Both cans were sprayed simultaneously through the single nozzle, thereby mixing the two components while spraying the mixture as a fine spray.

Figure 1A:
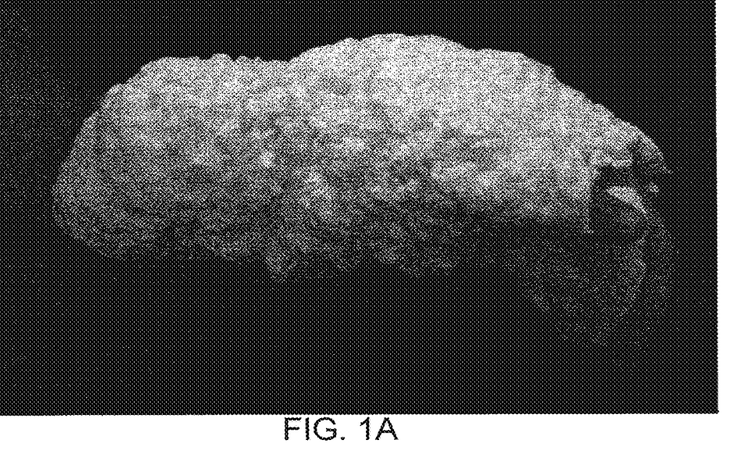
FIG. 1A shows a photograph of an example of a rigid foam cast of the present subject matter sprayed directly on the skin of the arm, wrist, and hand.
Figure 1B:
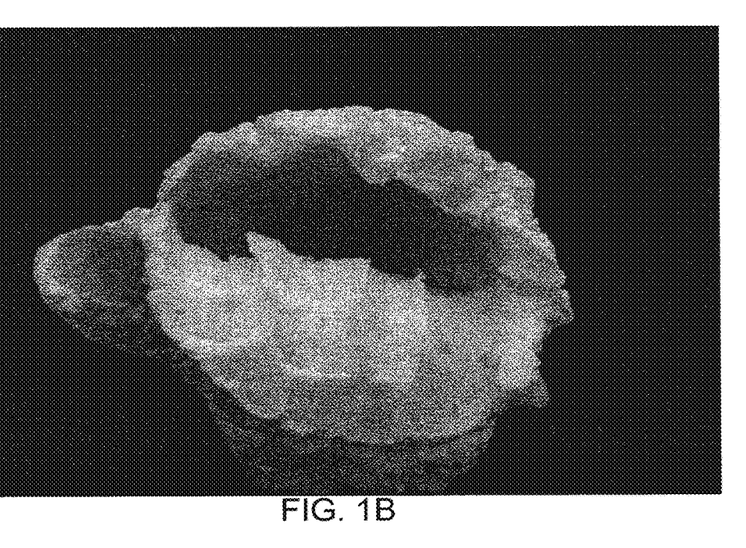

The extremity was first positioned so that a single continuous application of spray could be applied circumferentially to the entire extremity as needed. One single coat for the FROTH-PAK was then sprayed circumferentially on the extremity. FIG. 1A shows a paragraph of an example of the rigid foam cast of FROTH-PAK sprayed directly on the skin of the arm, wrist, and hand. FIG. 1B is a photograph of the cast in FIG. 1A after the arm was removed from the cast. An open-cell structure can be seen in FIG. 1B.

Example 2

Figure 2A:
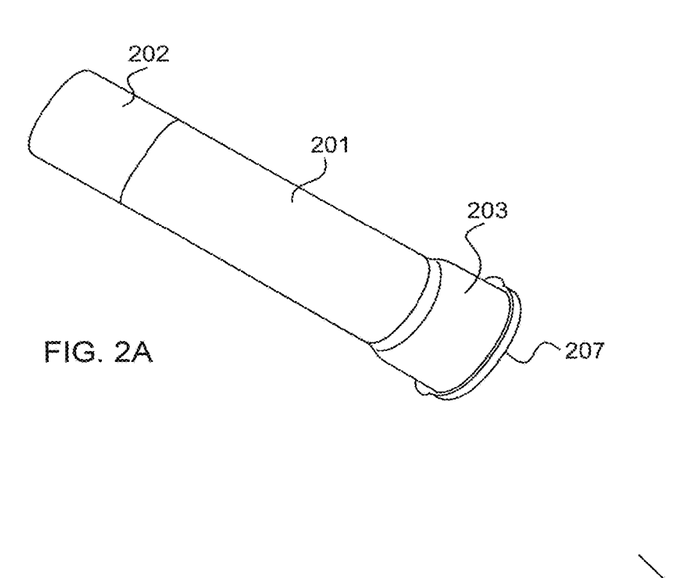
FIGS. 2A and 2B schematically show one embodiment of a kit of the present subject matter comprising a dispenser comprising a foamable composition of the present subject matter.
Figure 2B:
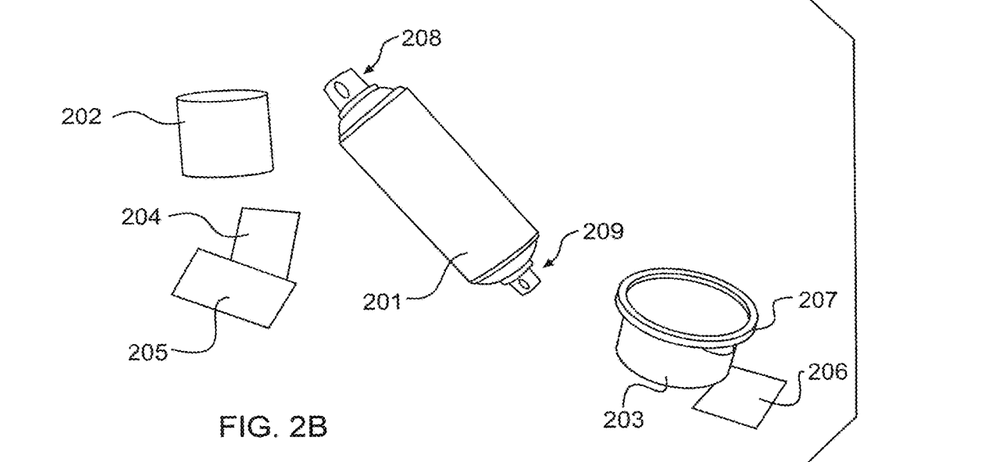

FIGS. 2A and 2B schematically show one example of a kit of the present subject matter comprising a dispenser (201) comprising a foamable composition of the present subject matter. A cap (202) may cover the foam dispenser nozzle. In this example, packages of antibiotic powder (204), granular hemostatic agent (205), and a medical dressing (206) for dressing open wounds are provided in the kit, such as being placed under one or more end caps (202,203), or affixed to the outside of the dispenser (201). A first cap (202) covers a spray foam nozzle (208), and second cap (203) covers a nozzle or applicator (209) for dispensing a liquid irrigant, such as saline. Also in this example, the second detachable cap (203) is a walled-form having one open end and the other end of the cap is open and fitted with a detachable cover (207). This walled-form cap (203) can be placed around a selected wound area on the injured limb or extremity to prevent foam from covering the wound area so that it can remain open to observation after the foam is dispensed to stabilize the injured limb or extremity. In one embodiment, the detachable cover (207) may be partially covered with foam either accidentally or deliberately to keep the cover in place, and the foam on the cover may then be easily removed later by the medical care provider to access the observation area formed by the walled-form.

Example 3

Figures 3A, 3B:
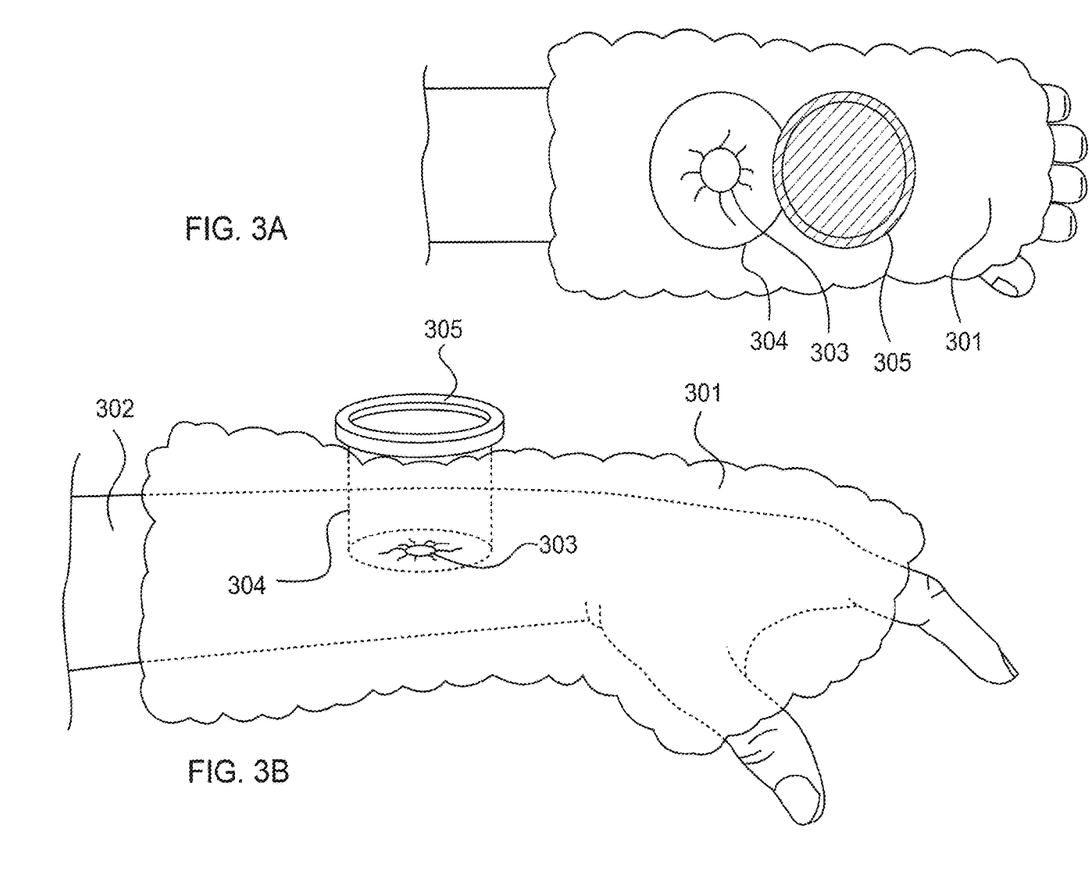

FIGS. 3A (top view) and 3B (side view) schematically show an example of a rigid foam cast (301) of the present subject matter on an injured extremity (302) having an open wound (303) and the cast comprising an open-ended walled-form (304) with an optional detachable cover (305). The walled form (304) and cover (305) are placed over the wound area before the rigid foam cast is sprayed on the injured extremity so that the wound can remain open to observation or access after the foam cast is applied to stabilize the injured limb or extremity. FIG. 3A, shows removal of the detachable lid (305) from the walled-form (304) so that the wound (303) can be accessed for observation and/or treatment.

Example 4

FIGS. 4A and 4B schematically show an example of a spine board of the present subject matter and a method of preparing and placing the spine board on the patient. A patient (401) requiring a spine board to be applied to that patient's back (402) will be placed. The foam (404) of the present subject matter is then applied to the patient's back (402) and/or the board or flat surface (403) and the patient is immediately rolled back onto the board or flat surface (403) before the foam sets. The foam is then allowed to set to sufficient rigidity (405). The patient and spine board may then be moved. The spine board may optionally further comprise one or more restraints (such as straps) for immobilizing the patient and/or securing the patient to the spine board.

Example 5

The Orthopedic Battle System (OBS) Kit: The base structure is a simple spray can and cap similar to any spray can. The can has two caps (blue and green) one at each end of the can. The can has two nozzles, one under each cap at each end. Under the blue cap is a nozzle that sprays simple normal saline irrigation. Under the green cap is a nozzle that sprays the foam. The can contains a two-component SPF, wherein each component is stored in its own separate container in the can. The two components are mixed while spraying both components simultaneously thru the nozzle under the green cap. Under the blue cap are two packets the size and shape of table sugar, each will contain a different powdered antibiotic, such as, for example, Tobramycin and Vancomycin. The green cap will have a re-sealable lid similar to a TUPPERWARE lid. Under this lid will be two packets of QUICK-CLOT, a granular chemical hemostatic agent. Under a wrapper attached to the body of the can is an impervious transparent self-adherent medical dressing wound cover (TEGADERM) for optionally covering larger open wounds if they are present. A simple to complex wound may be identified, the wound is first irrigated to remove contaminants, then antibiotics are sprinkled into the wound, if bleeding is an issue then QUIK-CLOT is applied to the bleeding wound. The green cap is placed over the open wounds and spray foam is applied around the lid and circumferentially around the extremity. Excess foam on the lid can later be removed to access the observation area. In less than 1 minute, the wound can be irrigated, antibiotics applied, bleeding controlled, and the fracture stabilized in a rigid foam splint all with one simple compact can kit.

Example 6

Emergency workers respond to an accident and a person is found to have a broken arm with a bone sticking out of the skin (compound fracture). The arm is evaluated for circulation and neurologic injury. The open wound is optionally:

irrigated with saline, treated with antibiotics, treated with a hemostatic agent to stop excess bleeding, and/or covered with a medical dressing. The arm and wound is then sprayed directly with a two-component SPF in a circumferential manner, the foam expands, dried and hardens within seconds. The person can then be transported to a hospital or medical clinic without further stabilizing the injured arm. The spray foam is in a one-time dose can contained both of the two-components in separate chambers. The can similar in size to a small can of hairspray that is easy to store and transport. Both components are automatically mixed at the time of application when sprayed from a single nozzle connected to both chambers.

Example 7

A pediatric patient is found to have a fractured leg requiring an immobilizing cast to allow proper bone healing. The leg is evaluated for circulation and neurologic injury, fracture reduction, and molding and then the leg is then sprayed directly with a two-component SPF in a circumferential manner, the foam expands, dries and hardens within seconds. In this example, the pediatric patient does not require a sedative or general anesthesia to permit application of the cast, which contrasts with other prior art casting methods which require sedation in order to have strength to weight ratio and is much lighter than conventional casts, permitting near normal motion. A dye color is added to the cast to enhance patient acceptance of the cast. The foam cast does not absorb urine and fecal matter as does the cast padding in prior art casts and methods; this reduces the number of cast changes and skin break down issues. Many pediatric fractures do not require manipulation just stabilization, therefore the quick-setting foams of the present subject matter can be quickly and easily applied.

Example 8

A patient with diabetes is found to have a fracture ankle requiring a cast to allow proper bone healing. However, diabetics have blood circulatory problems and have many problems in traditional casts due to the frequent formation of pressure sores, especially in diabetic feet. The ankle is positioned and SPF is sprayed onto the ankle, foot, and lower leg so that the foam easily and naturally follows the contours of the lower leg directly, and thereby creates an even stress load distribution which minimizes the likelihood of pressure sores developing on the treated extremity, and thereby promotes healing of sores that are already present.

Example 9

A surgical patient is being prepared for orthopedic reconstruction and replacement surgery, a lengthy surgical procedure requiring more than 2 hours on the operating table in one position. Such lengthy surgeries, requiring the patient to be in one position, are known to create pressure sores in specific body locations and must be padded. Traditional pads often do not perfectly conform to the patient's body and thereby leave the patient prone to developing pressure sores. The patient's body is positioned for surgery, and then the body location prone to sores is slightly lifted and SPF is sprayed onto the body location and the patient carefully lowered to the surgical mat so that the foam creates a pad that easily and naturally follows the contours of the body, and thereby creates an even stress load distribution which minimizes the likelihood of pressure sores developing on the padded body location.

It will be understood that many additional changes in the details, materials, steps and arrangement of parts, which have been herein described and illustrated to explain the nature of the present subject matter, may be made by those skilled in the art within the principle and scope of the present matter as expressed in the appended claims.

What is claimed is:

1. An apparatus for stabilizing an injured limb or extremity of a human or animal in an emergency or combat situation comprising:
    a spray can having a first nozzle at one end and a second nozzle at an opposite end;
    three containers disposed in the spray can;
    a two-component quick-cure spray polyurethane foam that sets to sufficient rigidity in less than 60 seconds after dispensing the foam on the injured limb or extremity wherein respective components of the two-component foam are disposed in first and second ones of the three containers and the foam is dispensed from the first nozzle;
    a liquid irrigant disposed in a third one of the three containers, the liquid irrigant being dispensed from the second nozzle and adapted to remove contaminants or foreign debris from a wound area on the injured limb or extremity before the foam is dispensed on the limb or extremity;
    a first cap that covers the first nozzle;
    a second cap that covers the second nozzle, the second cap being a walled-form having one open end and another end that includes a detachable cover.

2. The apparatus of claim 1, wherein the end with the detachable cover is one of open and transparent.

3. The apparatus of claim 2, further comprising one or more components to be applied to the injured limb or extremity before the foam is dispensed on the injured limb or extremity, the one of more components selected from the group consisting of: at least one package of comprising a cleaning irrigant; at least one package comprising a hemostatic agent; at least one package comprising an antibiotic agent; at least one package comprising an anesthetic agent; at least one package comprising a medical dressing for open wounds; and combinations thereof.

4. The apparatus of claim 3, wherein the antibiotic agent is one of Tobramycin, Vancomycin and a combination of Tobramycin and Vancomycin.

5. The apparatus of claim 3, wherein at least one of the one or more components is disposed in one of the first and second cap.

6. The apparatus of claim 3, wherein at least one of the one or more components is attached to a body of the spray can.

7. The apparatus of claim 1, wherein the foam is a quick-cure soy-based foam.

8. A method for in situ manufacture and placement of a spine board for stabilizing an injured patient comprising:
    rolling the patient to raise the back of the patient;
    placing a board or flat surface under the back of the patient;
    dispensing a foam that is sufficiently tack-free and in full strength in less than 60 seconds on the clothed or unclothed back of the patient, on the surface of the board or flat surface, or a combination thereof;
    rolling the back of the patient onto the board or flat surface before the foam has set, wherein the foam does not produce an amount of heat release that is painful or uncomfortable to the patient; and allowing the foam to harden into a spine board having sufficient rigidity in less than 60 seconds.

9. The method according to claim 8, wherein the foam is a quick-cure polyurethane foam or a quick-cure soy-based foam.

10. The method according to claim 8, wherein the board has one or more holes or depressions, an uneven surface, a textured surface, or a combination thereof.

11. A spine board for stabilizing an injured patient comprising a two-component quick-cure polyurethane foam that is sufficiently tack-free and in full strength in less than 60 seconds and configured to be applied onto the back of the patient and allowed to set while the foam on the patient's back is contacting a board or flat surface;

wherein the foam is configured to be applied directly on the skin or on the clothing of the patient and does not produce an amount of heat release that is painful or uncomfortable for the patient;

and further wherein the foam sets to sufficient rigidity in less than 60 seconds.

12. The spine board according to claim 11, wherein the foam is a quick-cure soy-based foam.

13. A method for in situ preparation and application of a compression bandage on an injured patient in an emergency or combat situation comprising:

spraying a foam that is sufficiently tack-free and in full strength in less than 60 seconds on the injured patient and covering the wound requiring a compression bandage, wherein the foam does not produce an amount of heat release that is painful or uncomfortable on the skin of the injured patient; and allowing the foam to harden in less than 60 seconds to a rigidity sufficient to stop or slow a flow of blood.

14. The method according to claim 13, further comprising applying one or more components to the injured patient before the foam is dispensed, the one or more components selected from the group consisting of: at least one cleaning irrigant; at least one hemostatic agent; at least one antibiotic agent; at least one anesthetic agent; at least one medical dressing for open wounds; and combinations thereof.

* * * * *

UNITED STATES PATENT AND TRADEMARK OFFICE
CERTIFICATE OF CORRECTION

PATENT NO. : 10,350,103 B2  
APPLICATION NO. : 15/168639  
DATED : July 16, 2019  
INVENTOR(S) : Kevin D. Martin It is certified that error appears in the above-identified patent and that said Letters Patent is hereby corrected as shown below:

On the Title Page

Delete "14 Claims, 4 Drawing Sheets" and insert --12 Claims, 4 Drawings Sheets--.

In the Claims

Column 19, Lines 11-23, cancel Claim 11 in its entirety.
Column 20, Lines 1-2, cancel Claim 12 in its entirety.
Renumber the remaining Claims 1-12 in present order.

Signed and Sealed this
Twenty-seventh Day of August, 2019

Andrei Iancu
*Director of the United States Patent and Trademark Office*